United States Patent
Maitra et al.

(10) Patent No.: US 8,545,821 B2
(45) Date of Patent: Oct. 1, 2013

(54) COSMETIC USE OF WATER-REDISPERSIBLE POWDERS

(75) Inventors: Prithwiraj Maitra, Randolph, NJ (US); Wendy Chan, Chestnut Ridge, NY (US)

(73) Assignee: Avon Products, Inc., New York, NY (US)

( * ) Notice: Subject to any disclaimer, the term of this patent is extended or adjusted under 35 U.S.C. 154(b) by 165 days.

(21) Appl. No.: 12/899,873

(22) Filed: Oct. 7, 2010

(65) Prior Publication Data

US 2011/0104091 A1  May 5, 2011

Related U.S. Application Data

(60) Provisional application No. 61/258,251, filed on Nov. 5, 2009.

(51) Int. Cl.
*A61K 8/81* (2006.01)
*A61K 31/74* (2006.01)

(52) U.S. Cl.
USPC .......................... 424/63; 424/78.02

(58) Field of Classification Search
USPC ................................. 424/63, 78.02
See application file for complete search history.

(56) References Cited

U.S. PATENT DOCUMENTS

| | | | | |
|---|---|---|---|---|
| 5,575,989 | A * | 11/1996 | Caskey | 424/62 |
| 6,169,130 | B1 | 1/2001 | Bodmeier et al. | |
| 6,281,282 | B1 * | 8/2001 | Breitenbach et al. | 524/556 |
| 6,706,805 | B2 | 3/2004 | Weitzel | |
| 6,709,508 | B2 * | 3/2004 | Dietrich et al. | 106/724 |
| 6,890,975 | B2 | 5/2005 | Weitzel | |
| 7,012,114 | B2 | 3/2006 | Bett et al. | |
| 2005/0084510 | A1 * | 4/2005 | Carson | 424/401 |
| 2009/0198017 | A1 | 8/2009 | De Fazio | |
| 2010/0087583 | A1 | 4/2010 | De Fazio | |

FOREIGN PATENT DOCUMENTS

WO  2008/011658 A1  1/2008

OTHER PUBLICATIONS

Acquos Dehydro 7660 Techincal Data Sheet, Dec. 22, 2006.
Acquos Dehydro 6150 Techincal Data Sheet, Dec. 22, 2006.

* cited by examiner

*Primary Examiner* — Blessing Fubara
*Assistant Examiner* — Jennifer Berrios
(74) *Attorney, Agent, or Firm* — David M. Joyal; Joan M. McGillycuddy

(57) ABSTRACT

Cosmetic compositions comprising water-redispersible polymers are provided, as well as methods for using such compositions in cosmetics that afford powder-to-liquid and moisture-resistant benefits. These cosmetics can provide easier portability, as well as long wear benefits when topically applied to the skin or hair.

22 Claims, No Drawings

COSMETIC USE OF WATER-REDISPERSIBLE POWDERS

FIELD OF INVENTION

The present invention relates generally to compositions for cosmetic application which comprise water-redispersible polymers and the use of such compositions to provide cosmetics having increased portability and long wear benefits.

BACKGROUND OF THE INVENTION

While consumers seek cosmetics that are conveniently portable and that provide long wear benefits, there remains a continuing need in the cosmetic industry for such products.

Water-redispersible powders have been used in the building and construction industries. A water-redispersible powder typically is composed of a macromolecular polymer in powder form, prepared from a liquid dispersion of the polymer through drying processes, such as spray drying. Generally, the powder readily re-dissolves in water to re-form a dispersion or emulsion. The re-constituted form can be used, for example, as an adhesive or protective coating, as it dries to form a membrane or film that can be flexible, adhesive, and climate resistant.

Water-redispersible powders, also referred to in the construction industry as "dry powder glues," currently find use as tile adhesives or tile grouts; in mortars, such as standard mortar mix, decorative mortars or concrete repair mortars; in finishes, such as white render finishes; in paints, such as mineral hydraulic paints, for exterior insulation or thermal insulation systems, as self leveling compounds, and as other binders and/or performance modifiers. The advantages of these water-free redispersible powders include improved storage stability, long shelf-life and longer open-time, reduced transport and storage costs, and greater flexibility in the preparation of end-use formulations, as well as increased workability, flow, adhesion, abrasion resistance and climate resistance of the reconstituted composition.

Specific examples from the construction industry include acrylic polymers, such as the vinyl acrylic copolymers sold by the company Acquos, Pty Ltd, Victoria, Australia, under the Trade names Dehydro™ 6150 and Dehydro™ 6480; or the styrene acrylic copolymers also sold by Acquos as Dehydro™ 7552 and Dehydro™ 7660. These polymers readily recombine with water, and dry to form opaque films that are characteristically tacky but flexible. For example, the Dehydro™ 6150 product re-disperses in water to produce a composition having the characteristics typical of a liquid vinyl acrylic dispersion, so that Dehydro™ 6150 can be used where a vinyl acrylic dispersion is needed but where the product is desired in powder form. The redispersible polymers of this product, however, or any other water-redispersible powders, have not been used in the cosmetic industry.

There remains a need in the cosmetic arts for cosmetic compositions affording the convenience and advantages of water-redispersible powders, where such compositions could afford increased portability and wear of cosmetic products. It is therefore an object of the invention to provide compositions and methods addressing these and other needs.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, it has surprisingly been found that cosmetic compositions comprising water-redispersible polymers provide improved portability and long wear benefits; and thus find use as desirable cosmetic products. One aspect of the instant invention relates to cosmetic compositions, typically substantially anhydrous compositions, comprising at least one water-redispersible polymer in a cosmetically acceptable vehicle. The compositions are typically provided in the form of a free-flowing powder. The water-redispersible polymer may comprise a copolymer of vinyl acetate ester and alkyl acrylate ester; and/or a copolymer of styrene and acrylate ester. In some embodiments, the polymer comprises a copolymer having the structure of Formula I:

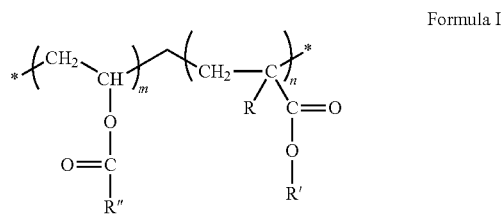

Formula I where R, R', and R", are each independently selected from aliphatic radicals, cycloaliphatic radicals, and aromatic radicals; and m and n are each integers independently selected from between 1 and 1,000. In some embodiments, the polymer comprises a copolymer having the structure of Formula II:

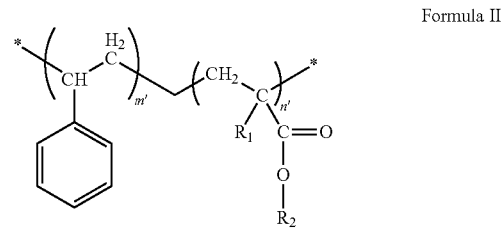

Formula II where R1 and R2 are each independently selected from aliphatic radicals, cycloaliphatic radicals, and aromatic radicals; and m' and n' are each integers independently selected from between 1 and 1,000.

The compositions of the invention are typically, but not necessarily, substantially anhydrous. They may be formulated for topical application to skin and may take the form of a color cosmetic, such as a foundation, and may include suitable amounts of coloring agents, such as pigments and pearlescents, and suitable amounts of fillers, such as talc, silica, and the like, as customary for such products. The cosmetic compositions may be in the form of a pressed-powder or a loose-powder, and more preferably in the form of a "powder-to-liquid" formulation, by which is meant a powder that can be reconstituted in the presence of a sufficient amount of liquid, typically water, to disperse the water-redispersible polymer. A topical composition for providing long-wear benefit as a foundation is also provided in a powder-toliquid formulation, preferably a substantially anhydrous formulation, where the composition comprises an effective amount of water-redispersible polymer(s) to provide long-wear benefit and a cosmetically acceptable vehicle.

Another aspect of the instant invention relates to methods for making or using cosmetic compositions comprising at least one water-redispersible polymer. In accordance with this aspect, the water-redispersible polymer is obtained by drying an aqueous dispersion of the polymer in the presence of at least one re-dispersing aid, for example where the re-dispersing aid is selected from the group consisting of a polyvinyl alcohol, a sulfonic acid polymer, a sulfated hydroxyl alkyl (meth)acrylate, an acetylated monoglyceride, and an alkalinizing agent, or a salt thereof. In accordance with another aspect, a method is provided for applying a topical composition to and integument (e.g., skin, hair, or nails) comprising providing a topical composition comprising at least one water-redispersible polymer; contacting the at least one water-redispersible polymer with a composition comprising water to disperse the redispersible polymer in water; and applying the reconstituted cosmetic formulation to the integument, typically the skin, such as the skin of the face. The composition comprising water may be, for example, water, and aqueous solution, an emulsion (e.g., W/O or O/W), or a "dry" composition which behaves like a particulate but comprises entrained or encapsulated water which is released upon combination with the topical composition.

In another aspect, a method is provided for applying a cosmetic composition to skin or hair, comprising applying a composition according to the invention, typically a substantially anhydrous composition, onto moist or wet skin or hair. The skin or hair may be wetted, for example, by applying water to the skin or hair; or by applying a composition comprising water to the skin or hair and causing water to be released from said composition comprising water. A composition according to the invention is then applied to the skin or hair while the skin or hair is still wet or moist. The topical composition may suitably be a foundation and the composition comprising water may take the form of a skin moisturizer, for example.

A method for providing long-wear benefit to a cosmetic composition is also provided comprising applying to the skin or hair a topical composition, typically a substantially anhydrous composition, comprising at least one water-redispersible polymer and contacting the water-redispersible polymer with an amount of water sufficient to maintain the water-redispersible polymer in a dispersed state; thereby renewing the topical composition on the skin or hair. The cosmetic composition may be, for example, a foundation and may be refreshed or renewed by dabbing water on the face using a sponge, cloth, or the like, or the water to renew the composition may be supplied by sweat or humidity.

Another aspect of the instant invention relates to methods for imparting long-wear benefits to cosmetic compositions, such as foundations, comprising adding to a cosmetic composition an amount of water-redispersible polymer effective to increase the wear of the topical composition when applied to skin or hair. Advantageously, the compositions provide long wear on oily skin. In some embodiments, the effective amount of water-redispersible polymer is from about 10 to about 50 weight %, or from about 13 to about 25 weight %, based on the total weight of the topical composition.

Another aspect of the instant invention relates to cosmetic kits. In some embodiments, a cosmetic kit is provided comprising (a) a first composition comprising at least one water-redispersible polymer in a cosmetically acceptable vehicle, the first composition typically, but not necessarily, being substantially anhydrous, and the first composition preferably being in the form of a powder; and (b) a second composition comprising water, the second composition preferably being water, and aqueous solution, an aqueous emulsion (e.g., W/O or O/W), and aqueous moisturizer, or a "dry" composition comprising entrained or encapsulated water which is releasable to the skin in an amount suitable for dispersing or reconstituting the polymer of the first composition. In preferred embodiments, the first composition is a color cosmetic, preferably a foundation.

These and other aspects of the invention will be better understood by reference to the following detailed description of the invention, and appended claims.

DETAILED DESCRIPTION

The present invention provides cosmetic formulations which may advantageously exist in the form of a solid (e.g., a powder, etc.) for ease of portability and use, and which may be reconstituted by addition of water, before or after application to the skin, to yield cosmetic composition that provides a long-wearing film on the skin or hair. The cosmetic compositions comprise one or more water-redispersible polymers in an amount effective to provide a long-wearing film on the skin or hair. The compositions are preferably in substantially anhydrous form and are readily reconstituted by contacting the one or more water-redispersible polymers with water, preferably with an amount of water sufficient to substantially hydrate and disperse the polymers, and provide extended wear benefits in cosmetic applications, in particular in colored cosmetic compositions topically applied to the skin and hair.

Water-Redispersible Cosmetic Compositions

In one aspect, the instant invention relates to a cosmetic composition comprising at least one water-redispersible polymer. A "water-redispersible polymer" is generally a macromolecular polymer that can be provided in powder form when dried and can surprisingly be re-dispersed in a suitable volume of water to re-form a stable, homogenous dispersion, in the absence of high sheer and without substantial flocculation. By "high sheer" is meant the degree of sheer generally produced in processes typically used to make homogenouos dispersions, including, but not limited to, bead milling, high pressure, and/or high sheer mixing. The "absence of high sheer" thus refers to levels of sheer generally experienced in a simple mixing process that may be accompanied by gentle mixing or stirring, but not involving, e.g., high strength grinding media, high speed rotation, high pressure pump systems and the like. Flocculation describes a process where macromolecules come out of a suspension in the form of floc or flakes. Water-redispersible powders in contrast form dispersions in water without substantial flocculation even in the absence of high sheer.

"Water-redispersible powders" refer to the powder forms of water-redispersible polymers, typically prepared from drying (e.g., spray drying) a liquid dispersion of the polymer. When added to water in an appropriate amount, a water-redispersible powder can readily reform the original dispersion from which it was obtained, providing for example the same or substantially the same original dispersion. Polymer dispersions are typically two-phase systems, comprising a dispersed colloidal polymer phase and an aqueous phase, which is the dispersion vehicle. The term "water-redispersible" is used interchangeably herein with "redispersible."

Suitable polymers include any macromolecular polymer capable of forming a redispersible powder. Suitable redispersible polymers include, for example, pure acrylic polymers (such as methylmethacrylate and alkyl acrylates, such as butyl acrylate); styrene-acrylic (such as based on styrene and alkyl acrylates, for example, 2-ethylhexyl-acrylate); vinyl acetate copolymers with alkyl acrylate or ethylene or maleates; and styrene-butadiene based polymers. More particularly, the polymer preferably contains two or more monomers selected from styrene, methylmethacrylate, vinyl acetate, butadiene, n-butyl acrylate, 2-ethylhexyl-acrylate, ethylacrylate, methylacrylate, isopropylacrylate, vinyl propionate, dibutyl maleate, ethylene, tert-butyl acrylate, methacrylic acid, acrylic acid, acrylamide, methacrylamide, and hydroxyethyl methacrylate. As used herein "polymer" includes "copolymers."

The polymer may also contain within its polymerized units one or more re-dispersing aids, such as AMPS monomer (2-acrylaminod-2-methylpropanesulfonic acid) and/or sulfated hydroxyl alkyl (meth)acrylate based monomer, polymer, and/or salt thereof. The re-dispersing aid, when in the salt form, generally includes an alkali metal salt or alkaline earth metal salt, ammonium salt or organic amine salt, calcium or sodium salts, or combinations thereof. See, e.g., International Patent Application Publication WO 2008/011658, the contents of which are herein incorporated by reference. In some embodiments, the redispersing aid is an alkalinizing agent, that is an a compound than can increase the pH of a solution to which is it added. Such compounds include, by way of example and without limitation, ammonia solution, ammonium carbonate, diethanolamine, monoethanolamine, potassium hydroxide, sodium borate, pH buffering agents, ammonium hydroxide, sodium carbonate, sodium hydroxide, triethanolamine, trolamine, and the like. Aqueous polymer dispersions are much more complex than organic polymer solutions and additives may be needed for to stabilize the dispersion. Examples of the additives include surfactants, e.g., which can stabilize the dispersion during preparation and storage; plasticizers, which can lower the minimum film formation temperature; and preservatives, which can protect the aqueous dispersion from microbial growth.

In some preferred embodiments, cosmetic compositions comprising vinyl acrylic and/or styrene acrylic copolymers are provided. For example, in some embodiments the water redispersible polymer comprises a copolymer of vinyl acetate ester and alkyl acrylate ester; and/or a copolymer of styrene and acrylate ester. In some preferred embodiments, the redispersible polymer comprises cellulose acetate phthalate (CAP). See, e.g., U.S. Pat. No. 6,169,160, the disclosures of which are herein incorporated by reference.

More preferred are acrylic or other polymers having a glass transition temperature (Tg) of less than about 50° C., even more preferably less than about 35° C., such as from about 0° C. to about 15° C.; from about 1° C. to about 10° C., or from about 5° C. to about 10° C. "Tg" or "glass transition temperature" of the polymer is the temperature at which the polymer becomes soft on heating or brittle on cooling. Below its Tg, the polymer is in a glassy state, with most bonds between the polymer chains intact. Above its Tg, these secondary non-covalent bonds between polymer chains become weak, and the polymer becomes soft and capable of deformation without fracture, as macromolecular chains slide past each other when a force is applied. See, e.g., Varshneya, "Fundamentals of inorganic glasses," Boston, Academic Press (1994). Tg can be measured, for example, using a Differential Scanning calorimeter instrument (DSC) or by other means, as known in the art. Redispersible polymers useful in the instant invention generally have glass transition temperatures below, preferably well below (i.e., at least 2.5° C., 5° C., or 10° C. below), body temperature (~35° C.), to allow formation of a flexible film on a body surface.

In some preferred embodiments, the cosmetic compositions comprise an acrylic polymer or other polymer that has a minimum film formation temperature (MFFT) of less than about 35° C., preferably well below (i.e., at least 2.5° C., 5° C., or 10° C. below) about 35° C., more preferably from about 0° C. to about 2° C. MFFT refers to the minimum temperature of a surface upon which the polymer composition forms a continuous film. The MFFT can be measured as known in the art, for example, using instrumentation such as a Film Forming Temperature Unit, such as a Rhopoint WP Film Forming Temperature Unit. Redispersible polymers useful in the instant invention generally have MFFTs below, preferably well below, body temperature (about 35° C.), to maintain a continuous film over a body surface.

In some embodiments, the water-redispersible polymer may be characterized as providing a solution upon dispersion in a fixed volume of water which is the same as or substantially the same as (e.g., ±5%, ±2.5%, ±1%, etc.) the original viscosity of an identical aqueous solution comprising the same amount of polymer and same volume of water from which the water-redispersible polymer was isolated.

In some particularly preferred embodiments, the cosmetic composition comprises at least one water-redispersible polymer selected from the polymers known as Dehydro™ 6150, Dehydro™ 6480, Dehydro™ 7552, and Dehydro™ 7660, which are commercially available from the company Acquos Pty Ltd, Victoria, Australia. Dehydro™ 7660 is particularly preferred, as are combinations of these different Dehydro products.

Dehydro™ 6150 and Dehydro™ 6480 are each copolymers based on vinyl acetate and alky acrylate esters, having the generalized structure of Formula I:

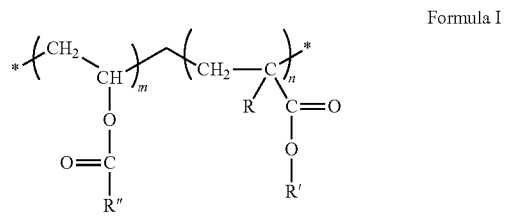

Formula I where R, R', and R", are each independently selected from hydrogen, an optionally substituted alkyl, acyl, aryl, alkene or alkyne group, a saturated or unsaturated, optionally substituted, or aromatic carbon-based ring, or a saturated or unsaturated, optionally substituted, heterocycle; and m and n (the number of each of the different repeating units) are integers selected independently of each other, where (m+n)>0.

In preferred embodiments, R, R', and R" are each independently selected from aliphatic radicals, cycloaliphatic radicals, and aromatic radicals. In preferred embodiments, m and n are each greater than or equal to 1, preferably between 1 and 10,000; more preferably between 1 and 5,000; and still more preferably between 1 and 1,000, selected independently of each other.

Dehydro™ 7552 and Dehydro™ 7660 are each copolymers based on styrene acrylate esters, having the generalized structure of Formula II:

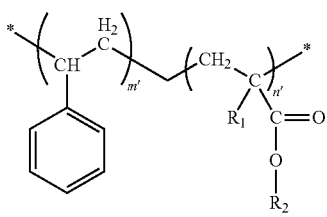

Formula II where R1 and R2 are each independently selected from hydrogen, an optionally substituted alkyl, acyl, aryl, alkene or alkyne group, a saturated or unsaturated, optionally substituted, or aromatic carbon-based ring, or a saturated or unsaturated, optionally substituted, heterocycle; and m' and n' (the number of each of the different repeating units) are integers selected independently of each other, where (m+n)>0.

In preferred embodiments, R1 and R2 are each independently selected from aliphatic radicals, cycloaliphatic radicals, and aromatic radicals. In preferred embodiments, m' and n' are each greater than or equal to 1, preferably between 1 and 10,000; more preferably between 1 and 5,000; and still more preferably between 1 and 1,000, selected independently of each other.

An aliphatic radical is an organic radical having at least one carbon atom, a valence of at least one and optionally a linear or branched array of atoms. Aliphatic radicals may include heteroatoms such as nitrogen, sulfur, silicon, selenium and oxygen or may be composed exclusively of carbon and hydrogen. Aliphatic radicals may include a wide range of functional groups, such as alkyl groups, alkenyl groups, alkynyl groups, halo alkyl groups, conjugated dienyl groups, alcohol groups, ether groups, aldehyde groups, ketone groups, carboxylic acid groups, acyl groups (for example, carboxylic acid derivatives such as esters and amides), amine groups, nitro groups, and the like.

A cycloaliphatic radical is a radical having a valence of at least one, and having an array of atoms, which is cyclic but which is not aromatic. A cycloaliphatic radical also may include one or more non-cyclic components. The cycloaliphatic radical may include heteroatoms such as nitrogen, sulfur, selenium, silicon and oxygen, or may be composed exclusively of carbon and hydrogen. A cycloaliphatic radical may include one or more functional groups, such as alkyl groups, alkenyl groups, alkynyl groups, halo alkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like.

An aromatic radical is an array of atoms having a valence of at least one and having at least one aromatic group. This may include heteroatoms such as nitrogen, sulfur, selenium, silicon and oxygen, or may be composed exclusively of carbon and hydrogen. Suitable aromatic radicals may include phenyl, pyridyl, furanyl, thienyl, naphthyl, phenylene, and biphenyl radicals. An aromatic radical may include one or more functional groups, such as alkyl groups, alkenyl groups, alkynyl groups, haloalkyl groups, haloaromatic groups, conjugated dienyl groups, alcohol groups, ether groups, thio groups, aldehyde groups, ketone groups, carboxylic acid groups, acyl groups (for example carboxylic acid derivatives such as esters and amides), amine groups, nitro groups, and the like.

The alkyl, acyl, aryl, alkene, and alkyne groups in formulas I and II are not particularly restricted in terms of size and number of carbon atom. However, in some embodiments, these groups will comprise from one to twenty carbon atoms, more typically, from one to ten carbon atoms, and more typical still, from one to sixe carbon atoms. The alkyl groups may include, without limitation, methyl, ethyl, propyl, butyl, pentyl, hexyl, and the like; the acyl groups include, without limitation, ethanoyl (acetyl), propanoyl, butanoyl, pentanoly, hexanoyl, heptanoyl, benzoyl, and the like; the alkenes include ethylene (vinyl), propylene (allyl), butylene (e.g., crotyl), pentylene, hexylene, and the like, and the alkynes, include ethynyl, propynyl, butynyl, penynyl, hexynyl, and the like. Each of these radicals may be substituted with one or more heteroatoms, typically selected from the groups consisting of halogen (F, Cl, Br, I), oxygen, sulfur, and nitrogen. In some embodiments, the alkyl, acyl, aryl, alkene, and alkyne radicals will optionally comprise from one to 20 heteroatoms, more typically from one to ten heteroatoms, and more typical still from one to five heteroatoms. Special mention may also be made of the case of perfluorinated, radicals. The carbon-based rings will usually comprise from three to twelve carbon atoms and the ring or ring system, typically from five to ten carbon atoms, and more typically will comprise five or six carbon atoms in the ring. Examples include, cyclopropane, cyclobutane, cyclopentane, cyclohexane, methylenecyclohexane, phenyl, and benzyl, and the like. The heterocycles will usually comprise from one to eleven carbon atoms in the ring or ring system, typically from two to eight carbon atoms, and more typically from three to five carbon atoms in the ring. The heterocyles will usually comprise from one to six, typically from one to four, and more typically from one to three heteroatoms in the ring, the heteroatoms typically being selected from the group consisting of oxygen, sulfur, and nitrogen. The carbon-based rings and the heterocycles may be optionally substituted with from one to ten heteroatoms, typically from one to six heteroatoms, and more typically from one to three heteroatoms, including halogen (F, Cl, Br, I), oxygen, sulfur, and nitrogen, and may also be optionally substituted with from one to five, typically from one to three, alkyl, acyl, aryl, alkene, and alkyne groups as defined above.

Needless to say, R, R', R", R1 and R2 are each selected so as to allow the resulting polymers to exhibit the property, of water-redispersability, as described herein and/or known in the art. Similarly, m, n, m' and n' are selected so that the resulting polymers are suitable for use as water-redispersible powders, as described herein and/or known in the art.

Based on the teachings provided herein, one of skill in the art can recognize other polymers typically used as water-redispersible powders in non-cosmetic arts, including for example the construction and coatings industries, that will find use in the cosmetic compositions of the instant invention. For example, one of skill in the art can select redispersible polymers having appropriate Tg, MFFT and/or solubility suitable for one or more cosmetic applications described herein. Examples include polymers with glass transition temperatures below about 35° C., preferably about 10° C. or less; and/or with an MFFT less than about 35° C., preferably about 2° C. or less. Tg, MFFT and other characteristics can be found or determined by one of skill in the art. Tg, for example, can be measured using a DSC; MFFT can be measured with a Rhopoint WP Film Forming Temperature Unit.

Additional specific examples of suitable redispersible polymers can be found, for example, in U.S. Pat. No. 7,012,114; U.S. Pat. No. 6,709,508; U.S. Pat. No. 6,890,975; and U.S. Pat. No. 6,169,130, as well as Intl App. Pub. No. WO 2008/011658, which are hereby incorporated by reference. Several of these aqueous polymer dispersions, and the water-redispersible powders obtainable from them by drying, are known in the construction and coatings industries, and are available commercially.

The water-redispersible polymers for cosmetic use in the instant invention can be prepared in a conventional manner, preferably by an emulsion polymerization process. The dispersions used may or may not be stabilized with an emulsifier, or with a protective colloid, an example being polyvinyl alcohol. To prepare the water-redispersible polymer powders, the corresponding polymer dispersion is dried, preferably by means of spray drying.

The water-redispersible polymers for use in the instant invention can be obtained by polymerizing selected monomers by any method known in the art such as by an emulsion polymerization process or by a suspension polymerization process, preferably by the emulsion polymerization process. In the emulsion polymerization process, the polymerization temperature is generally from about 40° C. to about 100° C., or from about 60° C. to about 90° C. Where gaseous co-monomers such as ethylene or vinyl chloride are copolymerized, it is also possible to operate under pressure, generally between about 5 bar and about 100 bar.

The polymerization can be initiated with water-soluble or monomer-soluble initiators, or redox initiator combinations, that are customary for emulsion polymerization or suspension polymerization, respectively. Examples of water-soluble initiators are the sodium, potassium and ammonium salts of peroxodisulfuric acid, hydrogen peroxide, t-butyl peroxide, t-butyl hydroperoxide, potassium peroxo-diphosphate, tert-butyl peroxopivalate, cumene hydro-peroxide, isopropylbenzene monohydroperoxide, and azobisisobutyronitrile. Examples of monomer-soluble initiators are dicetyl peroxydicarbonate, dicyclohexyl peroxydicarbonate, and dibenzoyl peroxide. These initiators are used generally in an amount of from about 0.01 to about 0.5% by weight, based on the overall weight of the monomers. Redox initiators used are combinations of any of these initiators with reducing agents. Suitable reducing agents include, for example, the sulfites and bisulfites of alkali metals and of ammonium, like sodium sulfite, the derivatives of sulfoxylic acid, such as zinc or alkali metal formaldehyde sulfoxylates, for example, sodium hydroxymethanesulfinate, and ascorbic acid. The amount of reducing agent is preferably from about 0.01 to about 0.5% by weight, based on the overall weight of the monomers.

In order to control the molecular weight, it is possible to use regulating substances during polymerization. If regulators are used, it is normally in amounts of from about 0.01 to about 5.0% by weight, based on the monomers to be polymerized, and they can be metered in separately or as a premix with reaction components. Examples of such substances include n-dodecyl mercaptan, tert-dodecyl mercaptan, mercaptopropionic acid, methyl mercapto propionate, isopropanol, and acetaldehyde.

The techniques for preparing polymer dispersions are either emulsion polymerization with water-insoluble monomers, or physical preparation methods, which use an already synthesized polymer. In the latter technique, a polymer solution or -melt is emulsified and homogenized in an aqueous phase, and the polymer dispersion is obtained after evaporation of the solvent or cooling of the aqueous phase.

Resulting dispersions then can be dried to give water-redispersible polymers in powder form. Typically, the liquid dispersion is subjected to a drying process where water is removed by a suitable method, such as spray drying or freeze drying. Spray drying is a widely used method that can give a fine powder, which in preferred embodiments, need not be further processed. In some embodiments, redispersing aids are added to the liquid dispersion before spray drying, e.g., polyvinyl alcohols; sulfonic acid polymers and salts thereof, such as 2-acrylamido-2-methylpropanesulfonic acid (AMPS); or sulfated hydroxyl alkyl (meth)acrylate based monomer, polymer and salts thereof. In some embodiments, the redispersing aid is an alkalinizing agent, as described above. Some embodiments involve drying an aqueous polymer dispersion of a nonionic polymer containing an alkalinizing agent, present in an amount sufficient to aid the dispersion of the redispersible polymer to re-form an aqueous dispersion. In some embodiments where the redispersible polymer comprises CAP, acetylated monoglycerides may be used as a redispersing aid, e.g., added to aqueous CAP-dispersions.

In certain particularly preferred embodiments, the process provides a water-redispersible polymer known as Dehydro™ 6150, Dehydro™ 6480, Dehydro™ 7552, or Dehydro™ 7660, also commercially available from the company Acquos. Dehydro™ 7660 is particularly preferred, as are combinations of polymers from these different Dehydro products.

Cosmetic compositions having a the property of water-redispersability can be made by adding to the composition one or more water-redispersible polymers in an amount effective to impart water-redispersability to the composition. "Water redispersability" refers to the ability of a dry composition, e.g., a powder, to break down in water into primary particles, which are then rapidly dispersed in the water to form a stable, homogenous dispersion. A water-redispersible powder, prepared from drying a liquid dispersion of redispersible polymers, readily reforms the original dispersion without substantial flocculation when combined with the appropriate amount of water, to give the same or approximately or substantially the same original dispersion. Redispersion may take place almost instantaneously upon combination with water, or it may take less than a second, a few seconds, or a few minutes. The redispersion process may be aided by mechanical agitation (such as gentle shaking or stirring).), but without the use of high sheer. The term "water-redispersability" is used interchangeably herein with "redispersability."

Water-redispersability is distinct from the property of mere dispersability or solubility in water. Accordingly, in some embodiments, the redispersible polymers useful in the instant invention exclude water soluble or water dispersible polymers; and in some embodiments, cosmetic compositions comprising water-redispersible polymers or powders do not include water soluble or water dispersible polymers which are not water re-dispersible Water dispersible and water soluble polymers are described, for example, in U.S. Pat. Appl. Pub. No. 2006/0140895 to Avon Products, Inc, the disclosure of which is hereby incorporated by reference. In some embodiment, film forming polymers which are not water re-dispersible will comprise less than 5% by weight of the dry formulation and typically will comprise less than 1% of the dry formulation. In other embodiments, the compositions will be substantially free of film forming polymers that are not water-redispersible by which is meant that the compositions will have such minor amounts of such polymers, if any, that no measurable impact on the long-wearing attributes, substantivity, or comfort of the cosmetic film applied to the skin is detectable.

In some embodiments, cosmetic compositions comprising water-redispersible polymers afford long wear. The wear of a cosmetic compositions can be increased, for example, by adding to the composition one or more water-redispersible polymers in an amount effective to increase the wear of the composition. "Long wear" refers to the ability of a cosmetic composition to stay on for an extended period of time; and/or to retain the appearance of having been freshly or recently applied for an extended period of time. Such compositions can also be described as having good or effective staying power, in that they can resist transfer from the surface to which they are applied for an extended period of time, preferably under various conditions. In preferred embodiments, the long wear cosmetic compositions comprise a topical composition to be applied to the surface of skin or hair. "Long wear" is used interchangeably herein with "extended wear," "increased wear," or "longer wear."

Cosmetic compositions comprising an effective amount of water redispersible polymer(s) to exhibit water redisersability and/or long wear benefits are provided herein. In some embodiments, the polymer is in an amount from about 10% to about 60%, based on the total weight of the composition. In some embodiments, the polymers are in an amount of at least about 13%, at least about 14%, at least about 15%, at least about 20%, at least about 21%, or at least about 25%, based on the total weight of the composition. In some embodiments, the polymers are in an amount of no more than about 55%, no more than about 50%, no more than about 40%, no more than about 30%, or no more than about 25%, based on the total weight of the composition. In certain particularly preferred embodiments, the water-redispersible polymer comprises at least one polymer selected from Dehydro™ 6150, Dehydro™ 6480, Dehydro™ 7552, and Dehydro™ 7660, commercially available from Acquos, more preferably in an amount effective to impart water-redispersability to the cosmetic composition, where the composition is to be topically applied to skin or hair.

Cosmetic Formulations of Redispersible Polymers

The compositions according to the instant invention can be formulated in a variety of forms for topical application. The composition may be formulated in a variety of product forms suitable for application to the skin, hair, eyelashes, or eyebrows; or suitable for being combined with water (or a composition comprising water) to provide a form suitable for such application. In preferred embodiments, the composition is in powder form, for example, a pressed-powder, compact, or a loose-powder. The powder can be for use as various types of cosmetic products, including, e.g., foundations, such as foundations for the face; eye products, such as eye shadow, eyeliner and mascara; or lip products, such as lipstick or lip gloss; as well as, personal care products for the skin or hair. Non-powder forms of topical compositions include, for example, a lotion, cream, liquid, serum, spray, aerosol, cake, ointment, essence, gel, paste, patch, pencil, pomade, solution, towelette, mask, mousse, stick, foam, elixir, concentrate, or any other known in the cosmetic arts.

The compositions can comprise an effective amount of at least one water-redispersible polymer. An "amount effective" or an "effective amount" refers to the amount of redispersible polymer sufficient to impart the property of water redispersability to the formulated product. For example, the water-redispersible polymer may be present in an amount from about 1% to about 99% by weight, more typically from about 10% to about 60%, based on the total weight of the composition. In some embodiments, the polymers are in an amount of at least about 13%, at least about 14%, at least about 15%, at least about 20%, at least about 21%, or at least about 25%, based on the total weight of the composition. In some embodiments, the polymers are in an amount of no more than about 55%, no more than about 50%, no more than about 40%, no more than about 30%, or no more than about 25%, based on the total weight of the composition.

The compositions of the present invention can include a cosmetically acceptable vehicle. Suitable vehicles include any vehicle for cosmetic, drug or medicament that is suitable for use in direct, safe contact with human tissues or human hair. Such vehicles may take the form of any known in the art suitable for application to skin or hair and may include, without limitation, hydrocarbons, glycerin, C1-4 alcohols, fatty alcohols, fatty ethers, fatty esters, polyols, glycols, vegetable oils, mineral oils, liposomes, laminar lipid materials, silicone oils, and any combinations thereof.

For powder (solid) formulations, preferred vehicles include one or more "wet" binders, one or more dry binders, or any combinations thereof. By "wet" binder is meant a liquid composition, rather than an aqueous composition, as the powder formulation is preferable free of water and other volatile solvents. The wet binders are preferably anhydrous or substantially anhydrous. The powder cosmetic composition may comprise from about 1 to about 30% by weight, preferably from about 3 to about 25% by weight, and more preferably from about 5 to about 15% by weight wet binder (e.g., oils). The oil is preferably non-volatile and may be selected from esters, silicone oils, hydrocarbon oils, polyols (e.g., glycerin) and certain polymers, such as polyurethanes, acrylates and the like.

The compositions of the invention are preferably provided in substantially anhydrous form. By "substantially anhydrous" is meant that the amount of water present, if any, is less than the amount needed to re-disperse the re-dispersible polymer, and typically is less than about 5%, preferably less than about 2.5%, more preferably less than about 1%, and more preferred still less than about 0.5% by weight of the total composition.

Ester oils include any non-polar or low-polarity esters, including isostearyl neopentonoate, isostearyl hydroxystearate, octyldodecyl stearoyl stearate, glyceryl esters, coco-caprylate/caprate, caprylic/capric triglyceride, stero esters, PPG-1 isoceteth-3 acetate, and the like. Special mention may be made of those fatty acid esters commonly used as emollients in cosmetic formulations. Such esters will typically be the etherification product of an acid of the form $R3(COOH)1-2$ with an alcohol of the form $R4(OH)1-3$, where R3 and R4 are each independently linear, branched, or cyclic hydrocarbon groups, optionally containing unsaturated bonds, and having from 1 to 30 carbon atoms, preferably from 2 to 30 carbon atoms, and more preferably, from 3 to 30 carbon atoms, optionally substituted with one or more functionalities, including hydroxyl, oxa, oxo, and the like. Preferably, at least one of R3 and R4 comprises at least 10, and more preferably, at least 15, 16, 17, or 18 carbon atoms, such that the ester comprises at least one fatty chain. The esters defined above will include, without limitation, the esters of mono-acids with mono-alcohols, mono-acids with diols and triols, di-acids with mono-alcohols, and tri-acids with mono-alcohols.

Suitable fatty acid esters include, without limitation, butyl acetate, butyl isostearate, butyl oleate, butyl octyl oleate, cetyl palmitate, ceyl octanoate, cetyl laurate, cetyl lactate, cetyl isononanoate, cetyl stearate, diisostearyl fumarate, diisostearyl malate, neopentyl glycol dioctanoate, dibutyl sebacate, di-C12-13 alkyl malate, dicetearyl dimer dilinoleate, dicetyl adipate, diisocetyl adipate, diisononyl adipate, diisopropyl dimerate, triisostearyl trilinoleate, octodecyl stearoyl stearate, hexyl laurate, hexadecyl isostearate, hexydecyl laurate, hexyldecyl octanoate, hexyldecyl oleate, hexyldecyl palmitate, hexyldecyl stearate, isononyl isononanaote, isostearyl isononate, isohexyl neopentanoate, isohexadecyl stearate, isopropyl isostearate, n-propyl myristate, isopropyl myristate, n-propyl palmitate, isopropyl palmitate, hexacosanyl palmitate, lauryl lactate, octacosanyl palmitate, propylene glycol monolaurate, triacontanyl palmitate, dotriacontanyl palmitate, tetratriacontanyl palmitate, hexacosanyl stearate, octacosanyl stearate, triacontanyl stearate, dotriacontanyl stearate, stearyl lactate, stearyl octanoate, stearyl heptanoate, stearyl stearate, tetratriacontanyl stearate, triarachidin, tributyl citrate, triisostearyl citrate, tri-C12-13-alkyl citrate, tricaprylin, tricaprylyl citrate, tridecyl behenate, trioctyldodecyl citrate, tridecyl cocoate, tridecyl isononanoate, glyceryl monoricinoleate, 2-octyldecyl palmitate, 2-octyidodecyl myristate or lactate, di(2-ethylhexyl) succinate, tocopheryl acetate, and the like. Other suitable esters include those wherein R4 comprises a polyglycol of the form H—(O—CHR*—CHR*)n- wherein R* is independently selected from hydrogen or straight chain alkyl, including methyl and ethyl, as exemplified by polyethylene glycol monolaurate.

Salicylates and benzoates are also contemplated to be useful esters in the practice of the invention. Suitable salicylates and benzoates include esters of salicylic acid or benzoic acid with an alcohol of the form R5OH where R5 is a linear, branched, or cyclic hydrocarbon group, optionally containing unsaturated bonds, and having from 1 to 30 carbon atoms, preferably from 6 to 22 carbon atoms, and more preferably from 12 to 15 carbon atoms. Suitable salicylates include, for example, octyl salicylate and hexyldodecyl salicylate, and benzoate esters including C12-15 alkyl benzoate, isostearyl benzoate, hexyldecyl benzoate, benzyl benzoate, and the like. Other suitable esters include, without limitation, polyglyceryl diisostearate/IPDI polymeric copolymer, triisostearoyl polyglyceryl-3 dimer dilinoleate, polyglycerol esters of fatty acids, and lanolin, to name but a few.

The oil may also be a non-volatile silicone oil. Suitable silicone oils include linear or derivatives of the cyclic silicones such as polyalkyl- or polyarylsiloxanes, optionally comprising alkyl or alkoxy groups having from 1 to 10 carbon atoms. Representative silicone oils include, for example, capryl lmethicone, decamethylcyclopentasiloxane, decamethyltetrasiloxane, diphenyl dimethicone, dodecamethylcyclohexasiloxane, dodecamethylpentasiloxane, heptamethylhexyl-trisiloxane, heptamethyloctyltrisiloxane, hexamethyldisiloxane, methicone, methyl-phenyl polysiloxane, octamethylcyclotetrasiloxane, octamethyltrisiloxane, perfluorononyl dimethicone, polydimethylsiloxanes, and combinations thereof. The silicone oil will typically, but not necessarily, have a viscosity of between about 50 and about 3,000 centistokes (cSt), preferably between 100 and 1,000 cSt measured at 25° C.

In some embodiments, the silicone oil comprises phenyl groups, as is the case for the silicone oil methylphenylpolysiloxane, INCI name diphenyl dimethicone, commercially available from Shin Etsu Chemical Co under a variety of tradenames including F-5W, KF-54 and KF-56. Diphenyl dimethicones have good organic compatibility and can impart additional film-forming characteristics to the product. In some embodiments, the silicone oil will have a refractive index of at least about 1.3, preferably at least about 1.4, more preferably at least about 1.45, and more preferred still at least about 1.5, when measured at 25° C. Another suitable phenyl-functionalized silicone oil has the INCI name phenyltrimethicone and is sold under the trade name "DC 556" by Dow Corning. DC 556 has a refractive index of about 1.46. In some embodiments, the silicone oil is a fluorinated silicone; preferably a perfluorinated silicone (i.e., fluorosilicones). A preferred fluorosilicone is a fluorinated organofunctional silicone fluid having the INCI name perfluorononyl dimethicone. Perfluorononyl dimethicone is commercially available from Pheonix Chemical under the trade name Pecosil®.

The compositions may also comprise hydrocarbon oils, preferably a non-volatile hydrocarbon oil. Exemplary hydrocarbon oils are straight or branched chain paraffinic hydrocarbons having from 20 to 80 carbon atoms, including but not limited to tetradecane, tridecane, and the like. Preferred hydrocarbon oils are highly branched aliphatic hydrocarbons, including C20-40 isoparaffins and the like. Special mention may be made of the isoparaffins having the INCI names isohexadecane and isoeicosane.

Suitable hydrocarbon oils are commercially available from Presperse (Somerset, N.J.) under the Permethyl® line of oils, including without limitation Permethyl®98R (Polyisobutene/Isododecane), Permethyl®216C (C18-21 Alkane/C13-16 Isoparaffin), Permethyl®101 A (Isohexadecane), Permethyl®102A (Isoeicosane), Permethyl®104A (Polyisobutene), Permethyl®222C (C13-15Alkane/C12-20Isoparaffin), Permethyl®105A (Polyisobutene), Permethyl®246C (C18-21Alkane/Polyisobutene), Permethyl®284C (C15-19Alkane/C12-14Isoparaffin/Polyisobutene), and Permethyl®296C (C 12-14Isoparaffin/C18-21Alkane). Also suitable as hydrocarbon oils are polyalphaolefins, typically having greater than 20 carbon atoms, including C24-28 olefins, C30-45 olefins, hydrogenated polyisobutene, hydrogenated polydecene, polybutene, mineral oil, pentahydrosqualene, squalene, squalane, and the like. The hydrocarbon oil may also comprise higher fatty alcohols, such as oleyl alcohol, octyldodecanol, and the like.

Other suitable oils include without limitation castor oil, C10-18 triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, avocado oil, camellia oil, macadamia nut oil, turtle oil, mink oil, soybean oil, grape seed oil, sesame oil, maize oil, rapeseed oil, sunflower oil, cottonseed oil, jojoba oil, peanut oil, olive oil, and combinations thereof.

Dry binders are also contemplated to be useful in some embodiments of the instant invention. Dry binders will function as binding agents when the compositions are reconstituted with water but are otherwise in dry, solid form in the substantially anhydrous compositions. When present, the dry binder will typically comprise from about 0.01 to about 15% weight of the composition, preferably from about 1 to about 12% by weight, or from about 2 to about 9% by weight of the composition. Dry binders include, without limitation, zinc stearate and kaolin.

Non-powder cosmetic compositions of the instant invention may also be placed in cosmetically acceptable vehicles. The vehicles may take the form of any known in the art suitable for application to skin or hair and may include water (e.g., deionized water); vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and isohexadecane; silicone oils such as cyclomethicone, dimethicone, dimethicone cross-polymer, polysiloxanes and their derivatives, preferably organomodified derivatives; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; or any combinations or mixtures of the foregoing.

The vehicle may comprise an aqueous phase, an oil phase, an alcohol phase, a silicone phase, individually or as mixtures thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like, for example, having the appearance of a cream, gel or micro-emulsions. The emulsion may include an emulsifier, such as a nonionic, anionic or amphoteric surfactant.

The aqueous phase of the emulsion may include water, as well as one or more additional solvents, including lower alcohols, such as ethanol, isopropanol, and the like. The volatile solvent may also be a cosmetically acceptable ester such as butyl acetate or ethyl acetate; ketones such as acetone or ethyl methyl ketone; or the like.

The oil phase of the emulsion preferably has one or more organic compounds, including emollients; humectants (such as butylene glycol, propylene glycol, Methyl gluceth-20, and glycerin); other water-dispersible or water-soluble components including thickeners such as veegum or hydroxyalkyl cellulose; gelling agents, such as high MW polyacrylic acid, i.e. CARBOPOL 934; and mixtures thereof. The emulsion may have one or more emulsifiers capable of emulsifying the various components present in the composition.

Compounds suitable for use in the oil phase include without limitation, vegetable oils; esters such as octyl palmitate, isopropyl myristate and isopropyl palmitate; ethers such as dicapryl ether; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like. Suitable hydrophobic hydrocarbon oils may be saturated or unsaturated, have an aliphatic character and be straight or branched chained or contain alicyclic or aromatic rings. The oil-containing phase may be composed of a singular oil or mixtures of different oils.

Hydrocarbon oils include those having 6-20 carbon atoms, more preferably 10-16 carbon atoms. Representative hydrocarbons include decane, dodecane, tetradecane, tridecane, and C8-20 isoparaffins. Paraffinic hydrocarbons are available from Exxon under the ISOPARS trademark, and from the Permethyl Corporation. In addition, C8-20 paraffinic hydrocarbons such as C12 isoparaffin (isododecane) manufactured by the Permethyl Corporation having the tradename Permethyl 99ATM are also contemplated to be suitable. Various commercially available C16 isoparaffins, such as isohexadecane (having the tradename Permethyl®) are also suitable. Examples of preferred volatile hydrocarbons include polydecanes such as isododecane and isodecane, including for example, Permethyl-99A (Presperse Inc.) and the C7-C8 through C12-C15 isoparaffins such as the Isopar Series available from Exxon Chemicals. A representative hydrocarbon solvent is isododecane.

The oil phase may comprise one or more waxes, including for example, rice bran wax, carnauba wax, ouricurry wax, candelilla wax, montan waxes, sugar cane waxes, ozokerite, polyethylene waxes, Fischer-Tropsch waxes, beeswax, botanical waxes, microcrystalline wax, silicone waxes, fluorinated waxes, and any combination thereof.

The oil phase may comprise one or more volatile and/or non-volatile silicone oils. Volatile silicones include cyclic and linear volatile dimethylsiloxane silicones. In some embodiments, the volatile silicones may include cyclodimethicones, including tetramer (D4), pentamer (D5), and hexamer (D6) cyclomethicones, or mixtures thereof. Particular mention may be made of the volatile cyclomethicone-hexamethyl cyclotrisiloxane, octamethyl-cyclotetrasiloxane, and decamethyl-cyclopentasiloxane. Suitable dimethicones are available from Dow Corning under the name Dow Corning 200® Fluid and have viscosities ranging from 0.65 to 600,000 centistokes or higher. Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as hexamethyldisiloxane, octamethyltrisiloxane, decamethyltetrasiloxane, and dodecamethylpentasiloxane, to name a few.

Non-volatile silicone oils will typically comprise polyalkylsiloxanes, polyarylsiloxanes, polyalkylarylsiloxanes, or mixtures thereof. Polydimethylsiloxanes are preferred non-volatile silicone oils. The non-volatile silicone oils will typically have a viscosity from about 10 to about 60,000 cSt at 25° C., preferably between about 10 and about 10,000 cSt, and more preferred still between about 10 and about 500 cSt; and a boiling point greater than 250° C. at atmospheric pressure. Non limiting examples include dimethyl polysiloxane (dimethicone), phenyl trimethicone, and diphenyldimethicone. The volatile and non-volatile silicone oils may optionally be substituted will various functional groups such as alkyl, aryl, amine groups, vinyl, hydroxyl, haloalkyl groups, alkylaryl groups, and acrylate groups, to name a few.

Non-limiting emulsifiers include emulsifying waxes, emulsifying polyhydric alcohols, polyether polyols, polyethers, mono- or di-ester of polyols, ethylene glycol mono-stearates, glycerin mono-stearates, glycerin di-stearates, silicone-containing emulsifiers, soya sterols, fatty alcohols such as cetyl alcohol, acrylates, fatty acids such as stearic acid, fatty acid salts, and mixtures thereof. The preferred emulsifiers include soya sterol, cetyl alcohol, stearic acid, emulsifying wax, acrylates, silicone containing emulsifiers and mixtures thereof. Other specific emulsifiers that can be used in the composition of the present invention include, but are not limited to, one or more of the following: C10-30 alkyl acrylate crosspolymer; Dimethicone PEG-7 isostearate, acrylamide copolymer; mineral oil; sorbitan esters; polyglyceryl-3-diisostearate; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few. Additional emulsifiers are provided in the INCI Ingredient Dictionary and Handbook 11th Edition 2006, the disclosure of which is hereby incorporated by reference.

These emulsifiers typically will be present in the composition in an amount from about 0.001% to about 10% by weight, in particular in an amount from about 0.01% to about 5% by weight, and more preferably, from about 0.1% to about 3% by weight.

The water-in-silicone emulsion may be emulsified with a nonionic surfactant (emulsifier) such as, for example, polydiorganosiloxane-polyoxyalkylene block copolymers, including those described in U.S. Pat. No. 4,122,029, the disclosure of which is hereby incorporated by reference. These emulsifiers generally comprise a polydiorganosiloxane backbone, typically polydimethylsiloxane, having side chains comprising -(EO)m"- and/or —(PO)n"- groups, where EO is ethyleneoxy and PO is 1,2-propyleneoxy, the side chains being typically capped or terminated with hydrogen or lower alkyl groups (e.g., C1-6, typically C1-3). Other suitable water-in-silicone emulsifiers are disclosed in U.S. Pat. No. 6,685,952, the disclosure of which is hereby incorporated by reference herein. Commercially available water-in-silicone emulsifiers include those available from Dow Corning under the trade designations 3225C and 5225C FORMULATION AID; SILICONE SF-1528 available from General Electric; ABIL EM 90 and EM 97, available from Goldschmidt Chemical Corporation (Hopewell, Va.); and the SILWET series of emulsifiers sold by OSI Specialties (Danbury, Conn.).

Examples of water-in-silicone emulsifiers include, but are not limited to, dimethicone PEG 10/15 crosspolymer, dimethicone copolyol, cetyl dimethicone copolyol, PEG-15 lauryl dimethicone crosspolymer, laurylmethicone crosspolymer, cyclomethicone and dimethicone copolyol, dimethicone copolyol (and) caprylic/capric triglycerides, polyglyceryl-4 isostearate (and) cetyl dimethicone copolyol (and) hexyl laurate, and dimethicone copolyol (and) cyclopentasiloxane. Preferred examples of water-in-silicone emulsifiers include, without limitation, PEG/PPG-18/18 dimethicone (trade name 5225C, Dow Corning), PEG/PPG-19/19 dimethicone (trade name BY25-337, Dow Corning), Cetyl PEG/PPG-10/1 dimethicone (trade name Abil EM-90, Goldschmidt Chemical Corporation), PEG-12 dimethicone (trade name SF 1288, General Electric), lauryl PEG/PPG-18/18 methicone (trade name 5200 FORMULATION AID, Dow Corning), PEG-12 dimethicone crosspolymer (trade name 9010 and 9011 silicone elastomer blend, Dow Corning), PEG-10 dimethicone crosspolymer (trade name KSG-20, Shin-Etsu), dimethicone PEG-10/15 crosspolymer (trade name KSG-210, Shin-Etsu), and dimethicone PEG-7 isostearate.

The water-in-silicone emulsifiers typically will be present in the composition in an amount from about 0.001% to about 10% by weight, in particular in an amount from about 0.01% to about 5% by weight, and more preferably, below 1% by weight.

The oil-containing phase will typically comprise from about 10% to about 99%, preferably from about 20% to about 85%, and more preferably from about 30% to about 70% by weight, based on the total weight of the emulsion, and the aqueous phase will typically comprise from about 1% to about 90%, preferably from about 5% to about 70%, and more preferably from about 20% to about 60% by weight of the total emulsion. The aqueous phase will typically comprise from about 25% to about 100%, more typically from about 50% to about 95% by weight water.

Based on the teachings herein, a person skilled in the art will be able to select any of these vehicles, or any other materials described herein, and/or an amount thereof, such that the redesirable properties of the cosmetic compositions of the instant invention can be conserved.

In certain preferred embodiments, the cosmetic composition is a color cosmetic. For a color cosmetic product, the composition may comprise one or more colorants. For powder forms, for example, the colorant may comprise from about 0.1 to about 95% by weight of the total composition, preferably from about 0.5 to about 70% by weight, or more preferably from about 1.0% to about 25% by weight of the total composition. The dry powdered cosmetics may comprise, for example, from 0.5% to about 10% by weight pigments or other colorants, or from about 1.5% to about 5% by weight pigments or other colorants.

Suitable colorants, including pigments, pearlescent agents, lakes, and dyes, are well known in the art and are disclosed in the C.T.F.A. Cosmetic Ingredient Handbook, First Edition, 1988, the contents of which are hereby incorporated by reference. Organic pigments include, for example, FD&C dyes, D&C dyes, including D&C Red, Nos. 2, 5, 6, 7, 10, 11, 12, 13, 30 and 34, D&C Yellow No. 5, Blue No. 1, Violet No. 2. Exemplary inorganic pigments include, but are not limited to, metal oxides and metal hydroxides such as magnesium oxide, magnesium hydroxide, calcium oxide, calcium hydroxides, aluminum oxide, aluminum hydroxide, iron oxides ($\alpha$-Fe2O3, $\beta$-Fe2O3, Fe3O4, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides and zinc oxides and composite oxides and composite hydroxides such as iron titanate, cobalt titanate and cobalt aluminate. Other suitable colorants include ultramarine blue (i.e., sodium aluminum silicate containing sulfur), Prussian blue, manganese violet, bismuth oxychloride, talc, mica, sericite, magnesium carbonate, calcium carbonate, magnesium silicate, aluminum magnesium silicate, silica, titanated mica, iron oxide titanated mica, bismuth oxychloride, and the like. Further, one or more chroma-methicone colorants may be used, e.g., chroma-lite yellow-methocone, chroma-lite red-methicone, and chroma-lite black-methicone. The colorants may be surface modified with, for example, fluoropolymers, to adjust one or more characteristics of the colorant as described in, for example, U.S. Pat. Nos. 6,471,950, 5,482,547, and 4,832,944, the contents of which are hereby incorporated by reference. Suitable pearling pigments include without limitation bismuth oxychloride, guanine and titanium composite materials containing, as a titanium component, titanium dioxide, titanium lower oxides or titanium oxynitride, as disclosed in U.S. Pat. No. 5,340,569, the contents of which are hereby incorporated by reference. The compositions may also include glittering agents.

The compositions may be formulated for application to the hair and may include temporary, semi-permanent, and permanent hair dyes. These may be oxidative hair dyes or direct hair dyes.

Oxidative hair dyes typically comprise (i) an oxidizing agent, such as hydrogen peroxide, sodium perborate or persulfate, a bromate of sodium, calcium, or magnesium, sodium iodate, or the like, (ii) an alkalizing agent in an amount effective to obtain a pH in the range of about 9.5 to 10.5, and (iii) one or more dye intermediates which can react in the presence of the oxidizing agent to form a colored molecule. The dye forming intermediates include oxidative dye precursors (also known as a "base") and optionally color modifiers (or "couplers"). Suitable oxidative dye precursors include, without limitation, those disclosed in U.S. Pat. No. 7,449,029 to Nguyen, U.S. Pat. No. 7,458,995 to Daigo, U.S. Pat. No. 7,056,351 to Hammond et al., U.S. Pat. No. 6,740,129 to Tsujino et al., U.S. Pat. No. 4,865,619 to Junino et al., the disclosures of which are hereby incorporated by reference herein. The oxidizing agent is preferably present from about 0.1% to about 6% by weight of the composition and the dye forming intermediates collectively will typically comprise from about 0.001% to about 5% by weight of the composition.

Direct dyes include, without limitation, nitro dyes, anthraquinone dyes and acid dyes, oil-soluble dyes, basic dyes, and dyes of vegetable origin. When present, direct dyes will typically comprise from about 0.0001% to about 5% by weight of the composition. Specific direct dyes contemplated to by useful include, without limitation, those disclosed in U.S. Pat. No. 7,449,029 to Nguyen, U.S. Pat. No. 7,056,346 to Maubru, U.S. Pat. No. 7,458,995 to Daigo, U.S. Pat. No. 6,746,492 to Kawai et al., the disclosure of which is hereby incorporated by reference.

When formulating the compositions as hair dye products, it may be desirable to add and amount of thickener, such as a cationic or anionic polymer, sufficient to prevent the dye from running when applied to the hair. Particular mention may be made are acrylic acid polymers and copolymers. The thickener will typically be present from about 0.01% to about 4% by weight of the composition.

Cosmetically acceptable vehicles for the cosmetic powder compositions may also include various fillers and/or additional components. The cosmetic powder compositions of the instant invention may include from about 0 to about 80 weight % filler. Preferably, the powder cosmetic compositions include from about 5 to about 70 weight % filler, more preferably from about 10 to about 60 weight % filler. Suitable fillers include without limitation silica, treated silica, talc, zinc stearate, mica, kaolin, Nylon powders such as Orgasol™, polyethylene powder, Teflon™, starch, boron nitride, copolymer microspheres such as Expancel™ (Nobel Industries), Polytrap™ (Dow Corning) and silicone resin microbeads (Tospearl™ from Toshiba), and the like.

Additional colorant/powder fillers include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly (ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide; and stabilizers/rheology modifiers, for example, Bentone Gel and Rheopearl TT2. Other useful powders are disclosed in U.S. Pat. No. 5,688,831, and U.S. Pat. Appl. Pub. 2009/0142382, the disclosures of which are incorporated by reference.

The cosmetic powder compositions may optionally include preservatives. When present, the preservatives will include from about 0.01 to about 5% by weight, typically about 0.05 to about 4% by weight, and preferably about 0.1 to about 3% by weight % of the total composition.

The compositions of the invention may optionally comprise other active and inactive ingredients typically associated with cosmetic and personal care products, including, but not limited to, excipients, fillers, emulsifying agents, antioxidants, surfactants, additional film-formers, chelating agents, gelling agents, thickeners, emollients, humectants, moisturizers, vitamins, sodium ascorbyl/cholesteryl phosphate, minerals, viscosity and/or rheology modifiers, sunscreens, keratolytics, depigmenting agents, retinoids, hormonal compounds, alpha-hydroxy acids, trioxaundecanedioic acid, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, additional colorants, staining agents, depigmenting agents, hypopigmenting agents, preservatives, stabilizers, pharmaceutical agents, photostabilizing agents, optical diffusers, insect repellants, UV absorbers, UV blockers, antiperspirants, moisturizers, conditioners, and the like, and mixtures thereof. Based on the teachings herein, a person skilled in the art will be able to select any of these active or inactive ingredients, or any other materials described herein, and/or an amount thereof, such that the desirable properties of the cosmetic compositions of the instant invention can be conserved.

Examples of cosmetic formulations comprising water-redispersible polymers, in accordance with the instant invention, are provided in Examples 1-3, below. Example 1 provides four examples of loose-powder formulations comprising redispersible polymers. Example 2 provides three examples of pressed-powder formulations comprising redispersible polymers. Example 3 provides four examples of liquid formulations comprising redispersible polymers.

Cosmetic Use of Redispersible Compositions

Another aspect of the instant invention relates to cosmetic use of compositions comprising one or more water-redispersible polymers. Cosmetic compositions that are water-redispersible afford surprising and unique characteristics, desirable in cosmetic products. Such characteristics include the benefits of dry storage and ready reconstitution with water, which surprisingly translate to cosmetic products that provide easy portability and renewable long wear.

In some embodiments, the cosmetic composition comprising at least one water-redispersible polymer provides for easy portability. A water-redispersible cosmetic composition can be provided in a dry solid form, e.g., a powder, that is more compact, easier to store, and lighter to carry than its liquid counterpart. Further, water-redispersability allows for easy reconstitution of the dry product to a liquid form, where a consumer desires use of the product as a liquid. For example, a consumer may prefer to apply a topical composition as a liquid. A "topical composition" refers to a composition for use on an outer surface of the body, e.g., on the skin, e.g., on the skin of the face, lips, neck, hands, arms, stomach, back, legs, and the like; or for coating the surface of a keratin fiber, such as the hair, eyelashes, eyebrows, and the like, including false eyelashes and wigs. The cosmetic composition can be, for example, a foundation (such as a face foundation), a lip product (such as lipstick or lip gloss), an eye product (such as eye shadow, eyeliner or mascara), or other topical composition.

For example, a consumer may prefer to apply foundation as a liquid. The foundation composition may be provided in the form of a powder, such as a pressed-powder or loose-powder, that can quickly and easily form a liquid upon combination with water. Until its desired use, the consumer can enjoy the convenience of carrying and/or storing a more compact, lighter, and dry cosmetic product. Water-redispersability can thus provide the portability of powders with the application benefit of liquid foundation, e.g., as a powder-to-liquid foundation. Powder-to-liquid formulations for other cosmetic compositions, particularly topical compositions, are also provided in other embodiments.

Moreover, water-redispersability allows the consumer to carry a cosmetic product in circumstances where transporting a liquid formulation is not feasible. For example, Transportation Security Administration (TSA) regulations restrict air travel with liquids, or certain volumes of liquids. In some preferred embodiments, a consumer wishing to carry a cosmetic product onto a flight, and apply it as a liquid during or after the flight, will be able to carry the powder form of a cosmetic composition, activate with water when ready to use it, and topically apply the cosmetic in liquid form. Further, the powder form affords greater portability during travel than its liquid counterpart, which may be too heavy and/or voluminous to carry in a carry-on, handbag, purse, or the like.

The topical composition comprising at least one water-redispersible polymer can be combined with water, or a composition comprising water, to redisperse the polymer and form a liquid. The water may come from any source, preferably a hygienic source of water suitable for application to the human skin, eyelashes and/or hair. For example, in some embodiments, the water can be tap water, bottled water, water from a spray bottle or a moist wipe, water provided for drinking on flights, water from a drinking fountain, and the like. The water (or composition comprising water) may be combined with the cosmetic composition comprising water-redispersible polymer(s) before and/or during application of the cosmetic to the skin or hair. In some embodiments, water is provided along with the topical composition comprising redispersible polymer(s). Preferably the water is provided in a suitable amount in a separate compartment and supplied along with the topical composition as a cosmetic kit. Kits comprising compositions of the instant invention are described in more detail below.

In some embodiments, water is supplied by a second composition, such as a composition comprising water. "A composition comprising water" refers to a composition containing water in any form, where the water can be made available to redisperse (and/or disperse) a water-redispersible polymer as a liquid. Examples of compositions comprising water include, for example, moisturizers, or other moisture-rich or water-based compositions, as well as water itself. Moisturizers include any formulation for supplying water to the skin, such as a water-based lotion, gel, spray, cream, or the like.

In some embodiments, the topical composition comprising at least one water-redispersible polymer is applied to skin or hair following application of the composition comprising water to the skin or hair, preferably while the composition comprising water is still moist. The composition comprising water is still moist, for example, while at least some of the water from the composition remains on the skin or hair, and includes any point in time before the water from the composition has dried, substantially dried, or completely dried and evaporated from the skin or hair. For example, the composition comprising redispersible polymer(s) can be applied concurrently with applying the composition comprising water, immediately afterwards, or a short time afterwards. In some preferred embodiments, the topical composition comprising at least one redispersible polymer is a foundation, such as a foundation in powder form; and the composition comprising water is a water-based composition, such as a moisturizer. In some embodiments, the composition comprising water is provided along with the topical composition comprising redispersible polymer(s), for example, in a separate compartment of a cosmetic kit. Kits comprising compositions of the instant invention are described in more detail below.

In some embodiments, the water can be provided in the form of a second dry composition, for example, as a second powder. A dry composition can serve as a source of water, for example, where the water is encapsulated. In this context, "dry" means that the composition behaves in the manner typically associated with powders, for example, with the flow and handling properties typically associated with powders, despite the fact that encapsulated water is contained therein. The encapsulated water can be released, for example, in response to increased pressure, or other change(s) in conditions, becoming available to redisperse the water-redispersible polymer as a liquid. Different types of dry compositions comprising encapsulated water are known in the art and can serve as compositions comprising water in certain embodiment of the instant invention.

In some embodiments, for example, water may be encapsulated in a water-absorbent polymer; and the water may be released upon mechanical agitation, for example, as brought about by rubbing or mixing the second powder (or other dry composition comprising encapsulated water). The water-absorbent polymer may be any suitable polymer including, but not limited to, a wide variety of anionic, cationic, and non-ionic materials. Suitable polymers include, but are in no way limited to, acrylic polymers such as acrylamides, acrylates, and copolymers thereof; poly(alkylene oxides) such as poly(ethylene oxide); cross-linked polyethylene oxide co-polyurethane hydrogel; polyvinyl alcohols; ethylene maleic anhydride copolymer; polyvinylethers; polyacrylic acids; polyvinylpyrrolidones; polyvinylmorpholines; polyamines; polyethyleneimines; polyquaternary ammoniums; saponified copolymers of vinyl acetate-acrylic acid ester; and hydrolyzed copolymers of acrylonitrile or acrylamide, or crosslinked polymers of these hydrolyzed copolymers; partially-neutralized crosslinked poly(acrylic acid); natural based polysaccharide polymers such as methyl celluloses, carboxymethyl celluloses, carboxymethyl starches, hydroxypropyl celluloses, algins, alginates, carrageenans, acrylic grafted starches, acrylic grafted celluloses, chitin, chitosan, starch-acrylonitrile, neutralized graft polymers of starch-acrylic acid; and synthetic polypeptides such as polyaspartic acid, polyglutamic acid, polyasparagins, polyglutamines, polylysines, and polyarginines; as well as the salts, copolymers, cross-linked derivatives and mixtures of any of the foregoing polymers. Additional examples include those provided in US Appl. Pub. No. 2008/0044445, the disclosure of which is hereby incorporated by reference. The polymers may be hydrophilic (water soluble) or hydrophobic (water insoluble). Cross-linking hydrophilic polymers can increase the insolubility of the cross-linked compound. Additionally, cross-linked compounds have the capability of absorbing great amounts of water. The use-of so-called water superabsorbent polymers is contemplated.

Other examples of dry compositions comprising encapsulated water include suspensions of water-in-air that form powder-like compositions. When compressed or rubbed between two surfaces, such as between the hands or fingers, these dry powders can release their internal water. Such powders and improvements thereto are described, for example, in U.S. Appl. Pub. No. 2005/0084510, the contents of which are incorporated herein by reference. Such powder type water-in-air products are known in the art and are generally commercially available.

In some embodiments, the dry composition comprising encapsulated water is provided along with the topical composition comprising at least one redispersible polymer, for example, in the same or separate compartments of a cosmetic kit. Kits comprising compositions of the instant invention are described in more detail below. One of skill in the art will also recognize the need to maintain the water component encapsulated, so as to prevent crumbling and/or to improve stability and storage of the dry composition comprising encapsulated water. In some preferred embodiments, the topical composition comprising redispersible polymer(s) is a foundation in powder form; and the composition comprising encapsulated water is a second powder. The two powders can be mixed prior to application, e.g., mixed into one compartment and shaken, and/or mixed on the hand and rubbed, to release the encapsulated water, forming a liquid for topical application.

Long Wear Benefits

In some embodiments, the cosmetic composition comprising at least one water-redispersible polymer provides long-wear benefits, for example where the consumer desires to maintain a fresh look of a topical composition for an extended period of time. The time period may be a few hours, such as about 2, about 3, or about 4 hours, but is more typically at least about 6 hours, at least about 10 hours, at least about 12 hours, or at least about 18 hours, or at least about 24 hours or more. Long wear benefits are generally achieved by applying a cosmetic compositions described herein to pre- and/or post-moistened skin or hair; and/or by combining the composition with water and then applying.

In some embodiment, for example, long wear benefits can be achieved by combining the composition comprising redispersible polymer(s) with a composition comprising water, and then applying. For example, as described above, a powder composition comprising redispersible polymer(s) can be mixed with water to form a liquid, and the liquid then can be applied to skin or hair. This affords powder-to-liquid cosmetic products that combine the convenience of easy portability with the benefits of long wear. An Example demonstrating long wear properties of a topical composition that is first activated with water and then applied to the hands is provided below in Example 4.

Similar long wear benefits can be achieved, in some embodiments, by first applying a composition comprising water to the skin or hair, followed by a topical composition comprising redispersible polymer(s) while the composition comprising water is still moist on the skin or hair. For example, as described above, skin can be pre-moistened by applying a water-based composition such as moisturizer, followed by a topical composition comprising resdispersible polymer(s), such as a powder foundation. The water in the moisturizer on the skin can activate, as well as further re-activate, the redispersible polymer, e.g., reforming the flexible, adhesive film during wear to extend wear of the foundation. Again this affords powder-to-liquid cosmetic products that combine the convenience of easy portability with the benefits of long wear. Example 5 below demonstrates long wear properties of a topical composition applied to the face following moisturizer.

One measure of the wear of a topical composition involves a test for transfer resistance. "Transfer resistance" or "transfer resistant property" refers to the ability of an applied composition to adhere to and resist transfer from a surface to which the composition is applied. Transfer resistance can be measured, under various conditions, by any means known in the art, for example by standard transfer resistance tests, such as those described in Example 6 below.

In some preferred embodiments, the cosmetic composition comprises an amount of redispersible polymer(s) effective to increase the transfer resistance of the composition. Upon combination with water, redispersible polymers can form flexible, adhesive films on the surface to which they are applied, and the adhesion can increase transfer resistance. Transfer resistance can be improved under one or more conditions. For example, the transfer resistance of a cosmetic composition can be improved under dry conditions, so that less of the composition is removed from a surface when dry rubbed. Transfer resistance can also be improved under conditions involving water, oil, or other elements that typically act to smudge or remove makeup. This can provide a cosmetic with good staying power, where the cosmetic appears fresh and/or recently-applied after an extended period of time, even in the presence of water and/or oil. Particularly preferred embodiments provide cosmetic compositions comprising an amount of water-redispersible polymer effective to increase transfer resistance under one of more such conditions, e.g., as demonstrated in Example 6 below.

In certain preferred embodiments, for example, the topical composition shows increased transfer resistance to dry rubbing. Such compositions can find use, e.g., in anti-smudge long wear cosmetic products. Example 6 below demonstrates increased transfer resistance to dry rubbing using different compositions according to the instant invention.

In certain preferred embodiments, the topical composition shows increased transfer resistance in the presence of oil. Such compositions can find use, e.g., in anti-oil long wear cosmetic products. Anti-oil products may be particularly useful with respect to affording long wear benefits even on oily skin and/or hair. Oily skin can result, e.g., from overproduction of sebum and/or other skin secretions, and oily hair can likewise result from sebum-overproduction on the scalp. Example 6 below demonstrates increased transfer resistance in the presence of oil for different compositions according to the instant invention.

In certain particularly preferred embodiments, the topical composition shows increased transfer resistance under conditions involving water. Example 6 below demonstrates this resistance for different compositions according to the instant invention. Conditions involving water that typically act to fade or remove make up include sweating, e.g., sweating over the course of a day or sweating during a workout or other activity that causes increased sweat production. Water from tears or saliva, water encountered when swimming, or water from the atmosphere in high humidity climates, can also act to reduce the wear of topical compositions applied to the skin or hair. Preferred embodiments of the instant invention provide topical compositions comprising one or more redispersible polymers that show increased transfer resistance under such conditions, finding use, e.g., in anti-sweat or anti-moisture long wear cosmetic products. Particularly preferred embodiments provide topical compositions comprising one or more redispersible polymers that afford increased transfer resistance to water, and that further use the water to redisperse the polymer(s), so that the composition is renewed, as described in detail below.

Water-redispersability can allow an already-applied cosmetic composition to be renewed, and have its look re-freshened, upon subsequent combination with water, for example, where the water re-activates the film-forming and/or adhesive properties of the composition. That is, after applying a topical composition comprising at least one water-redispersible polymer to the skin or hair, the polymer can be allowed to recombine with water to extend its wear. Powder foundations in particular are known to generally lack good staying power, e.g., not lasting on the face for more than a few hours. A cosmetic composition comprising water-redispersible polymer(s), however, can be re-activated upon re-combination with water at one or more points in time during wear, e.g., every few hours or so, to re-form a liquid formulation. Reforming the liquid can act to renew a powder composition and extend its wear, for example, by renewing the flexible film that covers the skin (or hair) and/or renewing the composition's ability to adhere well to the skin (or hair) surface. This can further extend the staying power of the cosmetic.

The water used to renew and/or extend the wear of a composition described herein can come from any source. For example, any of the compositions comprising water described above can be used, including tap water, bottled water, a moisturizer or other water-based composition, a dry composition comprising encapsulated water, or any other source providing water that can be made available to redisperse a water-redispersible polymer already on the skin or hair. For example, as described above and demonstrated below in Example 5, water from a moisturizer previously applied to the skin can serve to activate, as well as to reactivate, preferably continually reactive, redispersible polymer(s), e.g., reforming the flexible, adhesive film during wear. Other sources of water for renewing and/or reactivating redispersible polymers include, without limitation, a moist wipe, e.g., dapped on the skin at one or more points in time during wear; or a spray of water (e.g., from a spray bottle or using one's fingertips) that also can be applied, e.g., at one or more points in time during wear.

In some embodiments, the water to renew and/or extend the wear of a topical composition of the instant invention comes from the skin of the wearer. For example, water from sweat or other skin secretions can mix with the water-redispersible composition on the wearer's skin. Sweat secreted throughout the day or during periods of exertion, such as during a workout, can act to renew the topical composition, as described above. Rather than acting to smudge, fade or remove makeup, sweat can instead provide positive benefits of renewing and/or extending the wear of topically-applied cosmetic compositions, increasing staying power of the cosmetic under such conditions. For example, the redispersible polymer can recombine with water from sweat to reform its flexible, adhesive film. In certain preferred embodiments, a composition comprising at least one water-redispersible polymer is used in a sweat-activated long wear foundation, where the foundation is in powder or liquid form. In certain preferred embodiments, a composition comprising at least one water-redispersible polymer is used in a sweat-activated long wear eye shadow, where the eye shadow is in powder or liquid form.

In some embodiments, the water to renew and/or extend the wear of a topical composition of the instant invention comes from the eyes of the wearer, for example, from tears. Water in tears and/or other eye fluids can mix with the water-re dispersible composition on, for example, the wearer's eyelashes, acting to renew the topical composition, as described above. Tears may be distributed over the eyelashes, for example, by the action of wiping away tears or rubbing one's eyes. Rather than acting to smudge, fade or remove makeup, tears can instead provide the benefit of renewing and/or extending the wear of topically-applied cosmetic compositions, increasing staying power of the cosmetics under such conditions. In certain preferred embodiments, a composition comprising at least one water-redispersible polymer is used in a tear-activated long wear eye product, such as a mascara or eyeliner.

In some embodiments, the water to renew and/or extend the wear of a topical composition of the instant invention comes from the mouth of the wearer, for example, from saliva. Water in saliva and/or other oral secretions can mix with the water-redispersible composition on, for example, the wearer's lips, acting to renew the topical composition, as described above. Saliva may be distributed over the lips, for example, by the action of licking one's lips and/or rubbing the lips together. Rather than acting as to smudge, fade or remove makeup, these actions can instead provide the benefits of renewing and/or extending the wear of topically-applied cosmetic compositions, increasing staying power of the cosmetics under such conditions. In certain preferred embodiments, a composition comprising at least one water-redispersible polymer is used in a saliva-activated long wear lip product, such as, for example a lipstick or lip gloss.

In some embodiments, the water to renew and/or extend the wear of a topical composition of the instant invention comes from the environment. For example, in humid climates, such as southeast Asia, the humidity of the atmosphere can serve as a source of water. Rather than acting to smudge, fade or remove makeup, humidity can instead provide the benefits of renewing and/or extending the wear of topically-applied cosmetic compositions, increasing staying power of the cosmetics under such conditions. In certain preferred embodiments, a composition comprising at least one water-redispersible polymer is used in a humidity-activated long wear foundation, eye product, or lip product, where the foundation, eye product, or lip product is in powder or liquid form.

In some embodiments, the water for renewing and/or extending the wear of a topical composition of the instant invention comes water encountered when swimming or engaging in other water-related activities. For example, the water may be from a pool, sea, lake, and the like. Rather than acting to smudge, fade or remove makeup, the water can instead act to renew and/or extend the wear of topically-applied cosmetic compositions, increasing staying power of the cosmetics under such conditions. In certain preferred embodiments, a composition comprising at least one water-redispersible polymer is used in a water-activated long wear foundation, eye product, or lip product, where the foundation, eye product, or lip product is in powder or liquid form.

Based on the teachings provided herein, one of skill in the art will recognize other cosmetic applications for the compositions described herein, and such applications are also contemplated as within the scope of the instant invention. For example, cosmetic compositions comprising at least one water-redispersible powder may also find use in personal care products, such as skin care products, for example, where it is desirable to carry such products in powder rather than liquid form; and/or where it is desirable to wear such products for extended periods of time, even under conditions of high humidity, increased sweat production, etc. Personal care products for the skin include, for example, a body lotion or body spray; personal care products for the hair included, for example, a leave-in conditioner or mousse. In preferred embodiments, the personal care product is a colored composition, e.g., an all-over bronzer.

The cosmetic compositions described herein find use in improved cosmetic products, including for example, powder-to-liquid foundations, anti-smudge, anti-oil long wear foundations, and moisture-activated long-wear foundations or lip products. The products can be provided individually or in any combination, including in kits with other compositions pertaining to their use, as described below.

Cosmetic Kits of Redispersible Polymers

Another aspect of the instant invention relates to cosmetic kits. Cosmetic kits can be prepared to include one or more compositions described herein. The cosmetic compositions can be provided in the form of a kit comprising (a) a first composition comprising at least one water-redispersible polymer in a cosmetically acceptable vehicle; and (b) a second composition comprising water. Optionally, the kit may include additional compositional components and/or instructions for the use of the product. Additionally, the kit may include a holder or container for each of the compositional component of the kit.

The first and second compositions can be provided in the same or separate compartments, preferably in separate compartments. A "compartment" as used herein refers to any structure capable of containing the first and/or second composition. For example, the first and/or second composition may be contained in a vial, vessel, bottle, tube, packet, package, pouch, sachet, bag, jar, or other container. The compartments may be made of any material, preferably a material that does not interact, or does not appreciably or does not significantly react, with the compositions contained therein. The compartments are preferably easy to open, dispense composition from and/or re-close. The compartment containing the first composition can be referred to as the first compartment; and the compartment containing the second composition can be referred to as the second compartment.

In certain preferred embodiments, the first composition comprising at least one water re-dispersible polymer is a cosmetic composition for topical application to the skin and/or hair. In particularly preferred embodiments, the first composition is in powder form and can be, for example, a foundation, such as a face foundation; a lip product, such as lipstick or lip gloss; an eye product, such as an eyeliner, eye shadow, or mascara, or other cosmetic product. Preferably, the first composition is a colored cosmetic composition.

In certain preferred embodiments, the second composition is water, such as water suitable for application to the hair or skin. The water can be provided in an amount suitable for combination with the first composition. An "amount suitable for combination" refers to an amount supplied in a compartment that reduces or eliminates the need to measure, or otherwise determine, an appropriate amount for combining with a given amount of another composition. For example, the water can be provided in a second compartment in an amount for redispersing the water-redispersible polymers of the first composition in the first compartment to form a liquid suitable for topical application. In some embodiments, the compartments provide the first and second compositions in amounts suitable for a single application, such that the entire (or near entire) contents of each compartment are mixed together to provide a liquid for one application to the skin or hair. In some embodiments, the compartments provide the first and second compositions in amounts suitable for N applications, and the compartments are made to indicate appropriate amounts to use with each application. N represents any number of applications, such as two, three, 10, 20, or more applications. The compositions may be mixed together in the first and/or second compartment, or in a third compartment provided for mixing. Mixing may involve shaking, stirring or other means of mechanical agitation. Alternatively, the first and second compositions may be mixed in the palm of the consumer's hand and then applied, e.g., to the face. Other packaging and/or mixing configurations will be apparent to those of skill in the art, in light of these teachings.

In some embodiments, additional water is provided, for example, in one or more additional components to allow for renewing the applied cosmetic. For example, water can be provided in a spray bottle or other device for applying water to the skin or hair in an amount suitable to re-disperse the polymers of the first composition while on the wearer's skin or hair. As described in detail above, this can re-activate or renew the formulation and thus increase the wear of the cosmetic product.

In certain preferred embodiments, the second composition is a water-based composition, such as a moisturizer. Similarly to that described above, the water-based composition or moisturizer may be provided in an amount suitable for use with a given amount of the first composition. For example, the compartments can provide the first and second compositions in amounts suitable for a single application, such that the entire (or near entire) contents of the second compartment, e.g., containing moisturizer, may be applied to the skin, such as the face, followed by applying the entire (or near entire) contents of the first compartment. A suitable amount for a single application can be the amount of moisturizer that supplies sufficient moisture to re-disperse the water-redispersible polymers of the first composition contained in the first compartment. In some embodiments, the compartments provide the first and second compositions in amounts suitable for N applications, and the compartments are made to indicate appropriate amounts to use with each application. Other packaging and/or mixing configurations will be apparent to those of skill in the art, in light of the teachings provided herein.

In certain preferred embodiments, the second composition is a dry composition comprising entrained or encapsulated water. Similarly to that described above, the dry composition comprising encapsulated water may be provided in an amount suitable for use with a given amount of the first composition. For example, the dry composition can be provided in a second compartment in an amount such that when combined with the first composition contained in a first compartment, sufficient water is released for re-dispersing the water-redispersible polymers of the first composition to form a liquid suitable for topical application. In some embodiments, the compartments provide the first and second compositions in amounts suitable for a single application, or more than one application, similarly as described above. Again, the compositions may be mixed together in the first and/or second compartment, or in a third compartment provided for mixing. Mixing may involve shaking, stirring, compressing, or other means of mechanical agitation to release the encapsulated water. Alternatively, the first and second compositions may be mixed and rubbed in the palm of the consumer's hand and then applied, e.g., to the face. Other packaging and/or mixing configurations will be apparent to those of skill in the art, in light of the teachings herein.

In some embodiments, additional amounts of the second composition are provided, for example, in one or more additional components to allow for renewing the applied cosmetic. For example, additional moisturizer can be provided in a spray bottle or other device for applying the moisturizer to the skin or hair in an amount suitable to re-disperse the polymers of the first composition while on the wearer's skin or hair. As described above, this can re-activate or renew the formulation and thus increase the wear of the cosmetic product.

In reconstituting the water-redispersible polymers with water, it is preferred, although not strictly necessary, to use a suitable volume of water and suitably vigorous agitation to achieve as nearly homogenous dispersion as practical such that localized regions of inhomogeneity are avoided, such as clumps and the like.

Specific examples of compositions according to the instant invention, along with experimental results demonstrating their long wear properties, are provided below. While examples and embodiments herein may be described individually, it will be readily apparent to those of skill in the art that various embodiments can be combined in any number of feasible ways and such combinations also are contemplated as being within the scope of the instant invention.

EXAMPLES

Example 1

Loose-Powder Formulations Comprising Redispersible Polymers

Table 1 provides four cosmetic compositions (identified as 1, 2, 3, and 4) comprising redispersible polymers (Dehydro™ 6150, Dehydro™ 6480, and/or Dehydro™ 7552) in loose-powder formulations, in accordance with the instant invention, where the amount of each component is listed in weight percentage of the entire formulation.

TABLE 1

| Ingredient | 1 | 2 | 3 | 4 |
|---|---|---|---|---|
| Dehydro ™ 6150 | 5 | 15 | 20 | — |
| Dehydro ™ 6480 | 5 | 5 | — | 25 |
| Dehydro ™ 7552 | 6 | 5 | 5 | — |
| Filler | 34.4 | 31.7 | 31.6 | 34.9 |
| Dry Binder | 41.7 | 37 | 37.1 | 34 |
| Wet Binder | 4.6 | 3.5 | 3.5 | 3.4 |
| Pigment | 2.9 | 2.4 | 2.4 | 2.3 |
| Preservative | 0.4 | 0.4 | 0.4 | 0.4 |

Example 2

Pressed-Powder Formulations Comprising Redispersible Polymers

Table 2 provides four cosmetic compositions (identified as 5, 6, 7, and 8) comprising redispersible polymers (Dehydro™ 6150, Dehydro™ 6480, and/or Dehydro™ 7552) in pressed-powder formulations, in accordance with the instant invention, where the amount of each component is listed in weight percentage of the entire formulation.

TABLE 2

| Ingredient | 5 | 6 | 7 |
|---|---|---|---|
| Dehydro ™ 6150 | 5 | 5 | 3 |
| Dehydro ™ 6480 | 7 | 0 | 0 |
| Dehydro ™ 7552 | 2.1 | 10 | 10 |
| Filler | 32.9 | 32 | 33 |
| Dry Binder | 34.5 | 34.5 | 36.5 |
| Wet Binder | 12 | 12 | 12 |
| Pigment | 5.4 | 5.4 | 5.4 |
| Preservative | 1.1 | 1.1 | 1.1 |

Example 3

Non-Aqueous Liquid Formulations Comprising Redispersible Polymers

Table 3 provides four cosmetic compositions (identified as 9, 10, 11, and 12) comprising redispersible polymers (Dehydro™ 6150, Dehydro™ 6480, Dehydro™ 7552, and/or Dehydro™ 7660) in liquid formulations, in accordance with the instant invention, where the amount of each component is listed in weight percentage of the entire formulation.

TABLE 3

| Ingredient | 8 | 9 | 10 | 11 |
|---|---|---|---|---|
| Dehydro ™ 6150 | 5 | 5 | 8 | 5 |
| Dehydro ™ 6480 | 3 | — | — | 5 |
| Dehydro ™ 7552 | 7 | 7 | 7 | — |
| Dehydro ™ 7660 | — | 3 | — | 5 |
| Filler | 17.6 | 17.6 | 17.6 | 17.6 |
| Emulsifier | 0.5 | 0.5 | 0.5 | 0.5 |
| Aesthetic Modifier | 28 | 28 | 28 | 28 |
| Solvent | 30 | 30 | 30 | 30 |
| Pigment | 8.9 | 8.9 | 8.9 | 8.9 |
| Preservative | 0.4 | 0.4 | 0.4 | 0.4 |

Example 4

Hand Study Demonstrating Tong Wear with Redispersible Polymers

A hand study was conducted to test long wear properties of a cosmetic composition comprising water-redispersible polymers, in accordance with the instant invention, on the hands. The cosmetic composition (test composition) comprised Avon Mineral Powder foundation (shade Nude) mixed with Dehydro™ 7660 redispersible powder, such that the redispersible powder comprised 25% by weight of the total composition. Avon Mineral Powder foundation (shade Nude), without added redispersible polymers, was used as a control (the control composition).

The subject applied the control composition on her left hand, and then an equal amount of the test composition, activated with water, on her right hand. The foundations were worn on the hands over the course of a day, and periodically evaluated visually. It was observed that after 2 hours of wear, the control composition was no longer visible, while the test composition remained visible at this point and afterwards.

Accordingly, this experiment demonstrates the ability of a composition comprising water-redispersible polymers to extend wear and provide long wear benefits on the hands. This experiment also demonstrates that combining a cosmetic composition comprising redispersible polymers (the test composition) with water before application can provide long wear benefits for 2 hours and more post-application.

Example 5

Split-Face Study Demonstrating Long Wear with Redispersible Polymers

A split-face study was conducted to test long wear properties of a cosmetic composition comprising water-redispersible polymers, in accordance with the instant invention, on the face. The cosmetic composition (test composition) again comprised Avon Mineral Powder foundation (shade Nude) mixed with Dehydro™ 7660 redispersible powder. Avon Mineral Powder foundation (shade Nude), without added redispersible polymers, again was used as the control (the control composition).

One subject first applied moisturizer to her whole face; followed by applying the control composition on the right side and an equal amount of the test composition on the left side of her face. Initially, no difference was observed between the two sides of the subject's face. Nonetheless, at 2 hours, 3 hours, and 3.5 hours after applying the foundations, it was observed that the left side of the face retained more foundation than the right side.

Accordingly, this experiment demonstrates the ability of a composition comprising water-redispersible polymers to extend wear and provide long wear benefits on the face as well. This experiment also demonstrates the ability of a previously-applied moisturizer to supply the water for combination with the water-redispersible polymers in the test composition, for 2 hours, 3 hours and 3.5 hours post-application.

Example 6

Transfer Study Demonstrating Long Wear with Redispersible Polymers

A transfer study was conducted to test the transfer resistance properties of different cosmetic compositions comprising water-redispersible polymers, in accordance with the instant invention. Two test cosmetic compositions were prepared, one comprising Avon Mineral Powder foundation mixed with Dehydro™ 7660 redispersible powder, such that the redispersible powder comprised 25% by weight of the total composition (25% DPG test composition); and the other comprising Avon Mineral Powder foundation mixed with Dehydro™ 7660 redispersible powder, such that the redispersible powder comprised 50% by weight of the total composition (50% DPG test composition). "DPG" refers to "dry powder glue" and % DPG refers to the weight % of water-redispersible powder used in each test composition. The compositions were combined with water and applied to test surfaces. As before, Avon Mineral Powder foundation, without added redispersible polymers, was used as the control (the control composition).

Transfer resistance of the test and control compositions were tested under conditions of (A) dry rubbing using a control composition and 25% DPG and 50% DPG test compositions. The test and control compositions were further subjected to conditions of rubbing in the presence of (B) water and (C) artificial sebum.

The test compositions demonstrated greater transfer resistance to dry rubbing. On a scale of 1 to 5, with 1 being the worst transfer resistance, and 5 being the best, the control composition was rated 2, the 25% DPG test composition was rated 4, and the 50% DPG test composition rated a 5. The test compositions also demonstrated greater transfer resistance under the other two conditions, namely (B) water; and (C) artificial sebum. Further, the 50% DPG test composition showed even greater resistance to transfer under all three conditions compared to the 25% DPG test composition. Specifically, under conditions of rubbing in the presence of either water (B) or artificial sebum (C), the control composition was rated 1, the 25% DPG test composition was rated 3, and the 50% DPG test composition rated a 4. Thus the test compositions comprising redispersible powders showed much better resistance to transfer from a surface on which they were applied when subjected to (A) dry rubbing; (B) water; and (C) artificial sebum; and further, the test composition comprising 50%, rather than 25% redispersible powder by weight, showed even greater resistance. Moreover, the higher transfer resistance of the test compositions as compared to the control composition indicates that the test composition affords longer wear benefits.

Accordingly, this experiment demonstrates the ability of compositions comprising water-redispersible polymers to resist transfer and provide long wear benefits under conditions of dry rubbing, water, and sebum, conditions that may be expected to be encountered by a wearer during the course of wear. This experiment also demonstrates the ability of cosmetic compositions comprising water-redispersible polymers (the test compositions) to afford anti-smudge, anti-moisture, anti-sweat, and anti-oil properties, thus providing long wear and moisture-resistant benefits, including providing such benefits even to oily skin.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method of applying a topical composition to hair comprising the steps of:

Applying an anhydrous topical composition comprising a water-redispersible polymer to the skin or hair and then further applying to the same portion of skin or hair an amount of water sufficient to homogeneously disperse said water-redispersible polymer in an aqueous phase;

wherein the water-redispersible polymer is a copolymer of styrene and acrylate ester, which is obtained by drying an aqueous dispersion of the water-redispersible polymer in the presence of at least one re-dispersing aid, said re-dispersing aid selected from the group consisting of a polyvinyl alcohol, a sulfated hydroxyl alkyl(meth)acrylate, an acetylated monoglyceride, and an alkalinizing agent, or a salt thereof.

2. The method according to claim 1 wherein said polymer comprises a copolymer having the structure of Formula II:

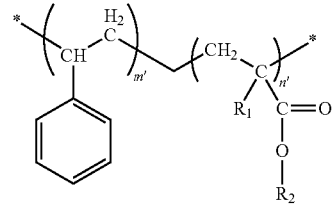

Formula II where R1 and R2 are each independently selected from aliphatic radicals, cycloaliphatic radicals, and aromatic radicals; and m' and n' are each integers independently selected from between 1 and 1,000.

3. The method according to claim 1 wherein said anhydrous topical composition is in the form of a pressed-powder or a loose-powder.

4. The method according to claim 1 wherein said anhydrous topical composition is a foundation.

5. The method according to claim 1 wherein said water is provided by a composition comprising encapsulated water and said encapsulated water is released upon combination with said topical composition.

6. The method according to claim 1 wherein the water-redispersible polymer is present in the anhydrous topical composition in an amount from about 5% to about 60% by weight, and wherein the anhydrous topical composition further comprises about 1% to about 25% by weight pigments or other colorants, from about 1% to about 95% by weight of a cosmetic filler, and optionally a wet and/or dry binder, where all percentages are based on the total weight of the composition, with the proviso that the combined percent by weight of all components in the composition do not exceed 100% by weight, wherein said anhydrous topical composition is in the form of a powder.

7. The method of claim 1, wherein said composition has improved transfer resistance to sweating.

8. The method of claim 1, wherein said composition has improved transfer resistance to humidity.

9. The method according to claim 1 wherein said anhydrous topical composition contains less than about 5% water by weight of the total composition.

10. The method according to claim 1 wherein said skin is oily skin.

11. The method according to claim 1 wherein said skin or hair is wet or moist.

12. A method of applying a topical composition to hair comprising the steps of:
Creating a reconstituted composition by combining an anhydrous topical composition comprising a water-redispersible polymer with a composition comprising an amount of water sufficient to homogenously disperse said water-redispersible polymer, and then applying the reconstituted composition to the hair or skin; wherein the water-redispersible polymer is a copolymer of styrene and acrylate ester, which is obtained by drying an aqueous dispersion of the water-redispersible polymer in the presence of at least one re-dispersing aid, said re-dispersing aid selected from the group consisting of a polyvinyl alcohol, a sulfated hydroxyl alkyl(meth)acrylate, an acetylated monoglyceride, and an alkalinizing agents, or a salt thereof.

13. The method according to claim 12 wherein said polymer comprises a copolymer having the structure of Formula II:

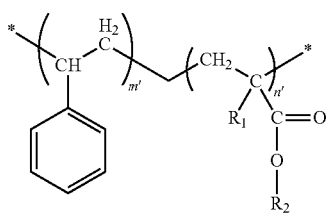

Formula II where R1 and R2 are each independently selected from aliphatic radicals, cycloaliphatic radicals, and aromatic radicals; and m' and n' are each integers independently selected from between 1 and 1,000.

14. The method according to claim 12 wherein said anhydrous topical composition is in the form of a pressed-powder or a loose-powder.

15. The method according to claim 12 wherein said anhydrous topical composition is a foundation.

16. The method according to claim 12 wherein said water is provided by a composition comprising encapsulated water and said encapsulated water is released upon combination with said anhydrous topical composition.

17. The method according to claim 12 wherein the water-redispersible polymer is present in the anhydrous topical composition in an amount from about 5% to about 60% by weight, and wherein the anhydrous topical composition further comprises about 1% to about 25% by weight pigments or other colorants, from about 1% to about 95% by weight of a cosmetic filler, and optionally a wet and/or dry binder, where all percentages are based on the total weight of the composition, with the proviso that the combined percent by weight of all components in the composition do not exceed 100% by weight, wherein said anhydrous topical composition is in the form of a powder.

18. The method of claim 12 wherein said composition has improved transfer resistance to sweating.

19. The method of claim 12 wherein said composition has improved transfer resistance to humidity.

20. The method according to claim 12 wherein said anhydrous topical composition contains less than about 5% water by weight of the total composition.

21. The method according to claim 12 wherein said skin is oily skin.

22. The method according to claim 11 wherein said skin or hair is wet or moist.

* * * * *